(12) United States Patent
Placik

(10) Patent No.: US 8,221,393 B1
(45) Date of Patent: Jul. 17, 2012

(54) MULTI-CHANNEL SURGICAL DRAIN AND ITS ASSOCIATED METHOD OF MANUFACTURE

(76) Inventor: Otto J. Placik, Arlington Heights, IL (US)

( * ) Notice: Subject to any disclaimer, the term of this patent is extended or adjusted under 35 U.S.C. 154(b) by 764 days.

(21) Appl. No.: 12/029,288

(22) Filed: Feb. 11, 2008

(51) Int. Cl.
 A61M 27/00 (2006.01)
 A61M 39/00 (2006.01)
(52) U.S. Cl. .................. 604/541; 604/35; 604/543
(58) Field of Classification Search ............ 604/313, 604/315–316, 543
See application file for complete search history.

(56) References Cited

U.S. PATENT DOCUMENTS

| | | | | |
|---|---|---|---|---|
| 2,286,462 | A * | 6/1942 | Chaffin | 604/43 |
| 3,590,820 | A * | 7/1971 | Nehra et al. | 604/268 |
| 3,730,035 | A * | 5/1973 | Bhatia | 83/54 |
| 4,398,910 | A * | 8/1983 | Blake et al. | 604/266 |
| 4,445,897 | A * | 5/1984 | Ekbladh et al. | 604/541 |
| 4,465,481 | A * | 8/1984 | Blake | 604/541 |
| 4,628,783 | A * | 12/1986 | Brownell et al. | 83/862 |
| 4,650,463 | A * | 3/1987 | LeVeen et al. | 604/43 |
| 4,692,153 | A * | 9/1987 | Berlin et al. | 604/171 |
| 4,925,452 | A * | 5/1990 | Melinyshyn et al. | 604/284 |
| 5,004,455 | A * | 4/1991 | Greenwood et al. | 604/43 |
| 5,100,395 | A | 3/1992 | Rosenberg | 604/284 |
| 5,116,310 | A * | 5/1992 | Seder et al. | 604/43 |
| 5,800,414 | A * | 9/1998 | Cazal | 604/523 |
| 5,891,111 | A | 4/1999 | Ismael | 604/541 |
| 5,947,953 | A * | 9/1999 | Ash et al. | 604/508 |
| 6,099,513 | A * | 8/2000 | Spehalski | 604/264 |
| 6,126,631 | A * | 10/2000 | Loggie | 604/43 |
| 6,478,789 | B1 * | 11/2002 | Spehalski et al. | 604/540 |
| 6,695,832 | B2 * | 2/2004 | Schon et al. | 604/544 |
| 6,866,657 | B2 * | 3/2005 | Shchervinsky | 604/266 |
| 6,881,211 | B2 * | 4/2005 | Schweikert et al. | 604/544 |
| 7,018,374 | B2 * | 3/2006 | Schon et al. | 604/544 |
| 7,125,402 | B1 * | 10/2006 | Yarger | 604/541 |
| D558,342 | S * | 12/2007 | Fujiwara et al. | D24/130 |
| 7,393,339 | B2 * | 7/2008 | Zawacki et al. | 604/43 |
| 7,658,735 | B2 * | 2/2010 | Spehalski | 604/543 |
| 2003/0153898 | A1 * | 8/2003 | Schon et al. | 604/544 |
| 2004/0176745 | A1 * | 9/2004 | Ferguson | 604/543 |
| 2005/0033222 | A1 * | 2/2005 | Haggstrom et al. | 604/43 |
| 2005/0234427 | A1 * | 10/2005 | Eder | 604/526 |
| 2009/0005762 | A1 * | 1/2009 | Nishtala et al. | 604/541 |

* cited by examiner

Primary Examiner — Jackie Ho
Assistant Examiner — Paula Craig
(74) Attorney, Agent, or Firm — LaMorte & Associates, P.C.

(57) ABSTRACT

A surgical drain tube assembly and its associated method of manufacture. The drain tube assembly has an extruded intake tube that defines multiple internal conduits. The intake tube has a first end and an opposite second end. The internal conduits run between the first end and the second end. The extruded intake tube contains multiple slices that run from the first end to a termination point. Each of the slices communicates with a different one of the internal conduits inside the intake tube. The internal conduits are therefore transformed into open grooves that are capable of draining fluids at any point along their lengths. The extruded intake tube can also be cut into separate arms that converge at the termination point. The intake tube is coupled to a single conduit collection tube that draws fluid from all the conduits of the intake tube.

7 Claims, 4 Drawing Sheets

MULTI-CHANNEL SURGICAL DRAIN AND ITS ASSOCIATED METHOD OF MANUFACTURE

BACKGROUND OF THE INVENTION

1. Field of the Invention

In general, the present invention relates to drain tubes that are used during surgical procedures. More particularly, the present invention relates to the physical structure of such surgical drain tubes and their methods of manufacture.

2. Prior Art Description

Whenever an invasive surgical procedure is performed on a patient, there is a possibility that fluid may collect in the surgical field opened during or after that operation. If the fluid is not drained, the surgical sight may not heal properly. If the fluid remains and becomes infected, the patient's life may be threatened.

It is for these reasons that surgical drains are used. A surgical drain is a device that is left in the operating field and drains fluids away as they form. For small surgical sights and/or surgical sights near the skin, passive surgical drains are often used. A "passive" drain is one in which only gravitational, capillary, or surface tension forces are used to move the collected fluids from the wounds, usually into the dressing. For large surgical fields and deep incisions, active surgical drains are typically used. An active surgical drain tube is one in which a vacuum source is provided to actively draw the fluid into a hermetically sealed container. Once the vacuum is applied, the container, drain and wound form a closed system with the liquid flowing in one direction only, namely to the container.

In an active surgical drain application, a plastic tube is traditionally used as the conduit for drawing fluids out of the patient's body. A problem associated with such drains is that the system can only draw fluid present at the tip of the tube. If fluid collects below the tip of the tube, that fluid cannot be drawn out of the body unless the drain is repositioned or a second drain tube is added.

One technique used to eliminate or reduce this problem is to position multiple drains in a wound, wherein each drain terminates at a different point in the wound. Such techniques are exemplified in U.S. Pat. No. 5,891,111 to Ismael, entitled Flexible Surgical Drain With A Plurality Of Individual Ducts. A problem associated with such multiple drain techniques is that the use of multiple drains requires a large opening leading into the wound. Furthermore, the many drains traversing the interior of the wound provides a physical obstruction to tissue that is trying to heal. The large opening leading to the wound and the obstructed wound site lead to higher risk of infection.

Another technique used to increase drain tube efficiency is to use a single tube that branches into multiple tubes within the wound. In this manner, a smaller incision can be made in the skin, thereby lowering the chance of infection. Furthermore, the tube elements within the wound can be perforated to increase the surface area on the tube able to draw fluids. Such prior art drain tubes are exemplified by U.S. Pat. No. 5,100,395 to Rosenberg, entitled Fluid Drain For Wounds.

Although such branched drain tubes are less intrusive than multiple individual tubes, such branched drain tubes still provide substantial obstructions to healing within the wound. Furthermore, the incision in the skin must be left large enough to accommodate the multi-prong head. Accordingly, the opening leading to the wound site is significant, as is the corresponding chance of infection.

A need therefore exists for a drain tube system that can draw fluid from a wide area of a wound site, yet can provide minimal obstructions to healing tissue within the drain site. Furthermore, a need exists for a drain tube that draws fluid effectively from many areas of a wound site, yet requires only a very small opening in the skin that leads to the would site.

These needs are met by the present invention as described and claimed.

SUMMARY OF THE INVENTION

The present invention is a surgical drain tube assembly and its associated method of manufacture. The drain tube assembly includes an extruded intake tube that defines multiple internal conduits. The intake tube has a first end and an opposite second end. The internal conduits run between the first end and the second end.

The extruded intake tube contains multiple slices that run from the first end to a termination point between the first end and the second end. Each of the slices communicates with a different one of the internal conduits inside the intake tube. The internal conduits are therefore transformed into open grooves that are capable of draining fluids at any point along their lengths.

The extruded intake tube can also be cut into separate arms that converge at the termination point. In this manner, different arms can be cut to different lengths and be used to drain different parts of a surgical field.

The intake tube is coupled to a single conduit collection tube that draws fluid from all the conduits of the intake tube.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention drain tube assembly can be configured to drain many types of wounds in different parts of the body, only one embodiment of the invention is illustrated. The exemplary embodiment is selected merely for illustration purposes and should not be considered a limitation upon the invention as it is defined by the claims.

Figure 1:
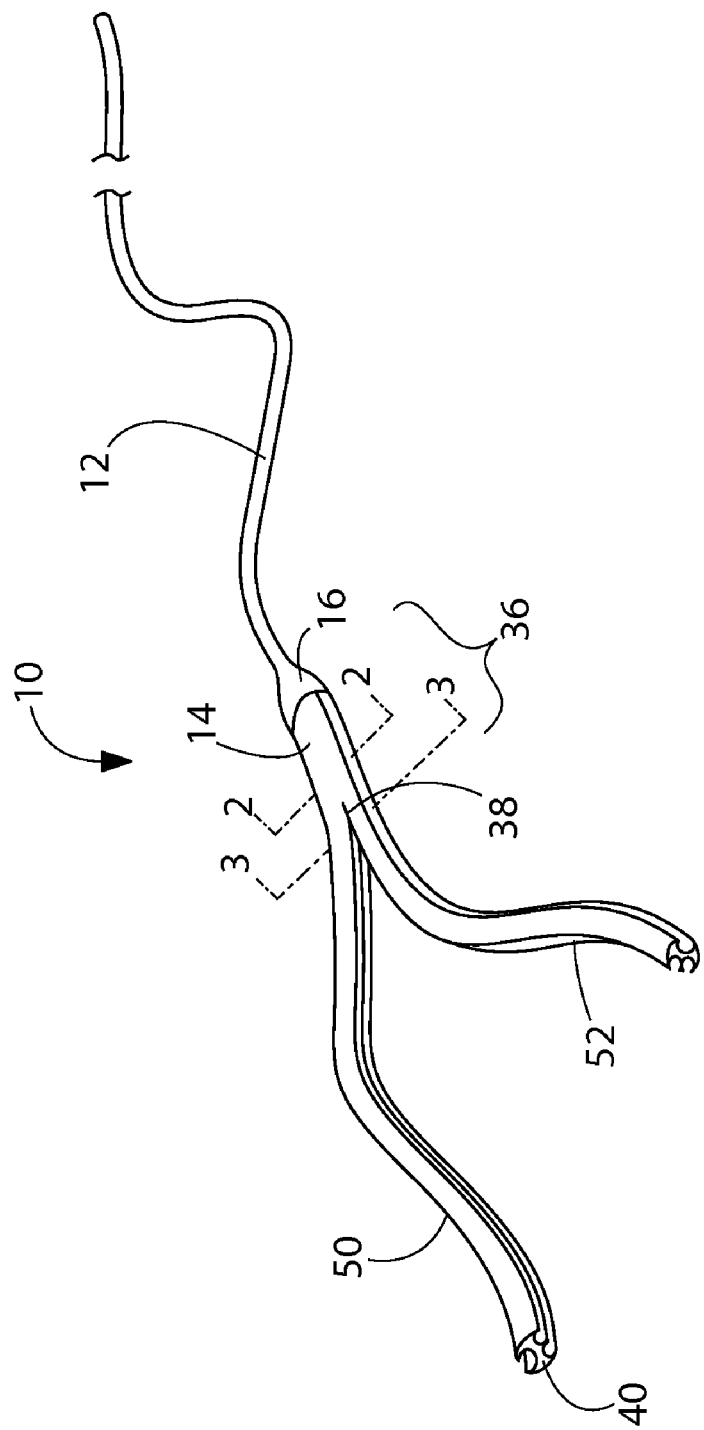
FIG. 1 is a perspective view of an exemplary embodiment of a surgical drain tube assembly.

Referring to FIG. 1, a drain tube assembly 10 is shown in accordance with the present invention. The drain tube assembly 10 is comprised of two extruded tubes. The two tubes include a collection tube 12 and an intake tube 14. The collection tube 12 is an ordinary piece of commercial plastic tubing. The collection tube 12 can be any length needed to reach an external suction machine. The collection tube 12 has a flared end 16 that is shaped to the distal end 18 of the intake tube 14. The intake tube 14 is preferably made from a plastic composition, such as silicon, that is far more flexible and soft than the traditional plastic tubing used for the collection tube 12.

Figure 2:
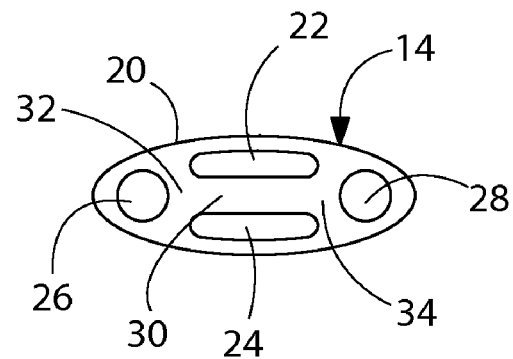
FIG. 2 is a cross-sectional view of the embodiment of FIG. 1, viewed along section line 2-2.

Referring to FIG. 2 in conjunction with FIG. 1, it can be seen that the intake tube 14 is an extruded tube that contains multiple internal conduits. In the shown embodiment, the intake tube 14 is extruded to contain four internal conduits that are contained within a continuous exterior wall 20. Those conduits include a top conduit 22, a bottom conduit 24, a left side conduit 26 and a right side conduit 28. The top conduit 22 and bottom conduit 24 are separated by a central partition 30. The left side conduit 26 is separated from the top and bottom conduits 22, 24 by a left side partition 32. Likewise, the right side conduit 28 is separated from the top and bottom conduits 22, 24 by a right side partition 34.

It will be understood that the use of an intake tube 14 with four internal conduits 22, 24, 26, 28, arranged in the manner illustrated is merely exemplary. The present invention can utilize tubing with conduits of other configurations as will later be described in more detail.

The intake tube 14 extends through a transition zone 36 from the flared end 16 of the collection tube 12 to a severance termination point 38. The transition zone 36 is preferably between one inch and six inches in length. When the drain tube assembly 10 is used on a patient, it is preferred that the drain tube assembly 10 enters a patient's body somewhere along the transition zone 36. In this manner, the incision used to enter the body need only be large enough to accommodate the cross-sectional profile of the intake tube 14. This is important if the intake tube 14 has a profile smaller than that of the collection tube 12 and/or the flared end 16 of the collection tube 12.

Figure 3:
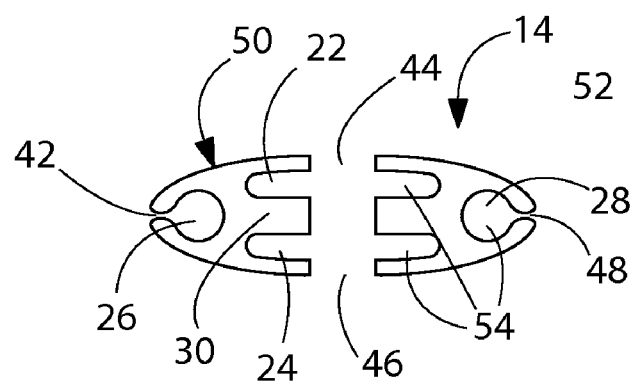
FIG. 3 is a cross-sectional view of the embodiment of FIG. 2, viewed along section line 3-3.

Referring to FIG. 3 in conjunction with FIG. 1, it can be seen that the intake tube 14 is sliced from its proximal end 40 down to the severance termination point 38. The intake tube 14 is sliced along multiple lines so that all four of the internal conduit 22, 24, 26, 28 are exposed along the entire length of each slice. The exterior wall 20 is sliced along four lines to accommodate exposing the four internal conduits 22, 24, 26, 28. The first severance line 42 is made in the exterior wall 20 at the apex of the left side conduit 26. Likewise the second, third and fourth severance lines 44, 46, 48 are cut in the exterior wall 20 at the apex of the top, bottom and right side conduits 22, 24, 28, respectively.

In addition to the exterior wall 20 being cut, the central partition 30 that separates the top conduit 22 from the bottom conduit 24 is cut down its center. This divides the intake tube 14 into two separate arms 50, 52. The arms 50, 52 are initially provided at equal lengths. However, a surgeon can cut the arms 50, 52 to different lengths if such a configuration better fits a wound.

The left arm 50 contains the cut left side conduit 26 and half the top and bottom conduits 22, 24. The right arm 52 contains the cut-open right side conduit 28 and the opposite halves of the top and bottom conduits 22, 24. Accordingly, each of the arms 50, 52 of the intake tube 14 defines three open grooves 54.

The open grooves 54 take on fluid at any point along their lengths. Each of the open grooves 54 leads to the transition zone 36 of the intake tube 14 beyond the severance termination point 38. The transition zone 36 leads to the collection tube 12, which leads to a vacuum source (not shown). It will therefore be understood that any fluid that enters into one of the grooves 54 on one of the arms 50, 52 of the intake tube 14, will migrate through the grooves 54 until that liquid is drawn out of the body and into the collection tube 12.

The present invention, therefore, provides a drain tube assembly 10 that has multiple arms 50, 52 that are capable of collecting fluid at any point along their lengths. Furthermore, the arms 50, 52 are made from a single extruded tube and, when combined, are no thicker than the single extruded tube. The parts being no greater than the whole.

Figure 4:
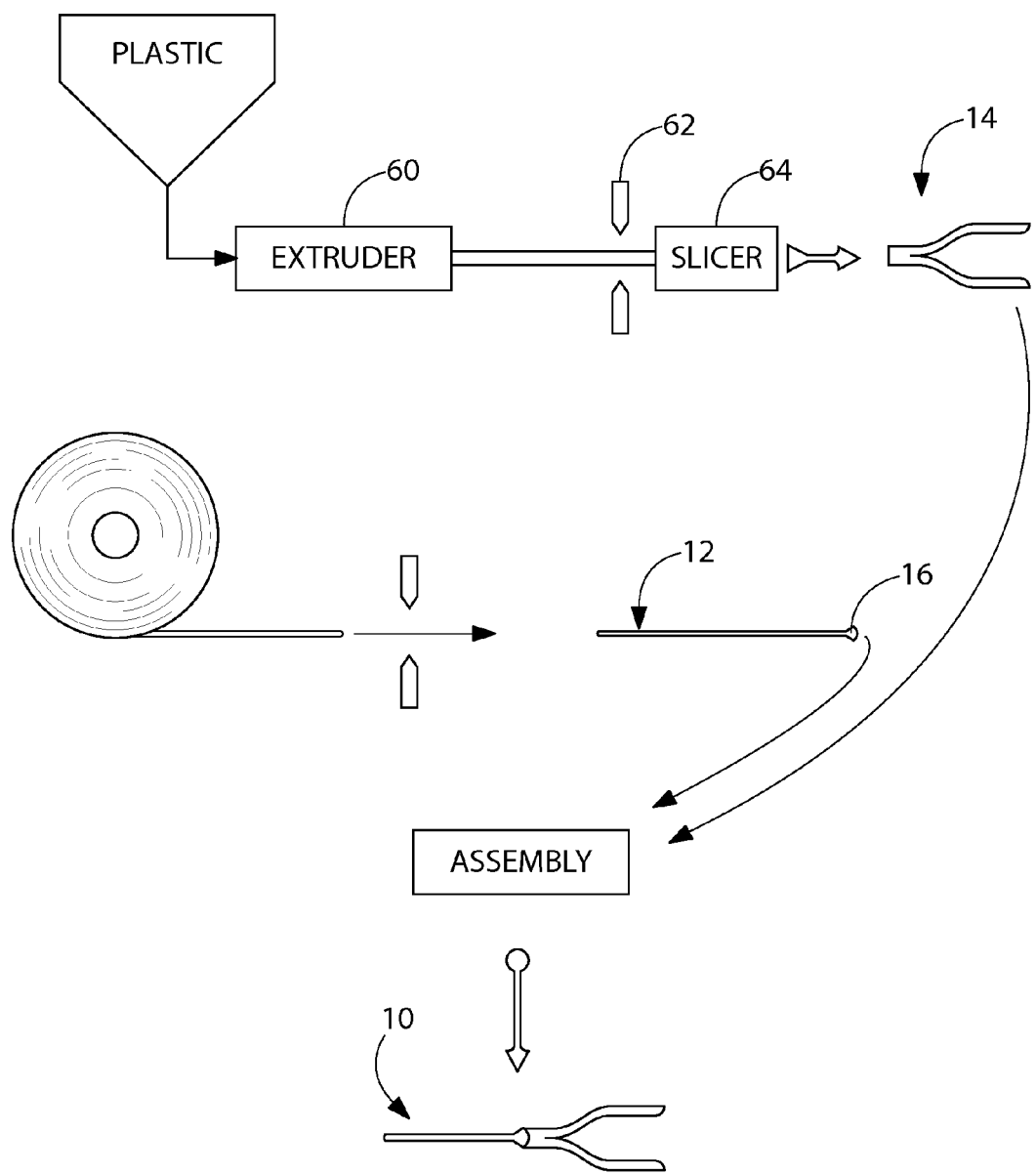
FIG. 4 is a schematic illustrating an exemplary method of manufacture.

Referring to FIG. 4, it can be seen that to make the present invention drain tube assembly 10, the intake tube is passed through an extruder 60 and is extruded into a desired tube shape having multiple interior conduits. Once the initial tube is formed, it is fed through a series of cutters. The tubing is drawn past a stationary slicer 64. This slices the lines of severance into the tubing. A secondary chopping blade 62 then cuts the tubing to length, therein forming the intake tube 14 previously described.

Ordinary tubing is cut to length and is flared at one end to form the collection tube 12. The intake tubing 14 is then inserted into the flared end 16 of the collection tube 12, where it is bonded in place with either adhesive or a heat weld. This creates the drain tube assembly 12.

Figure 5:
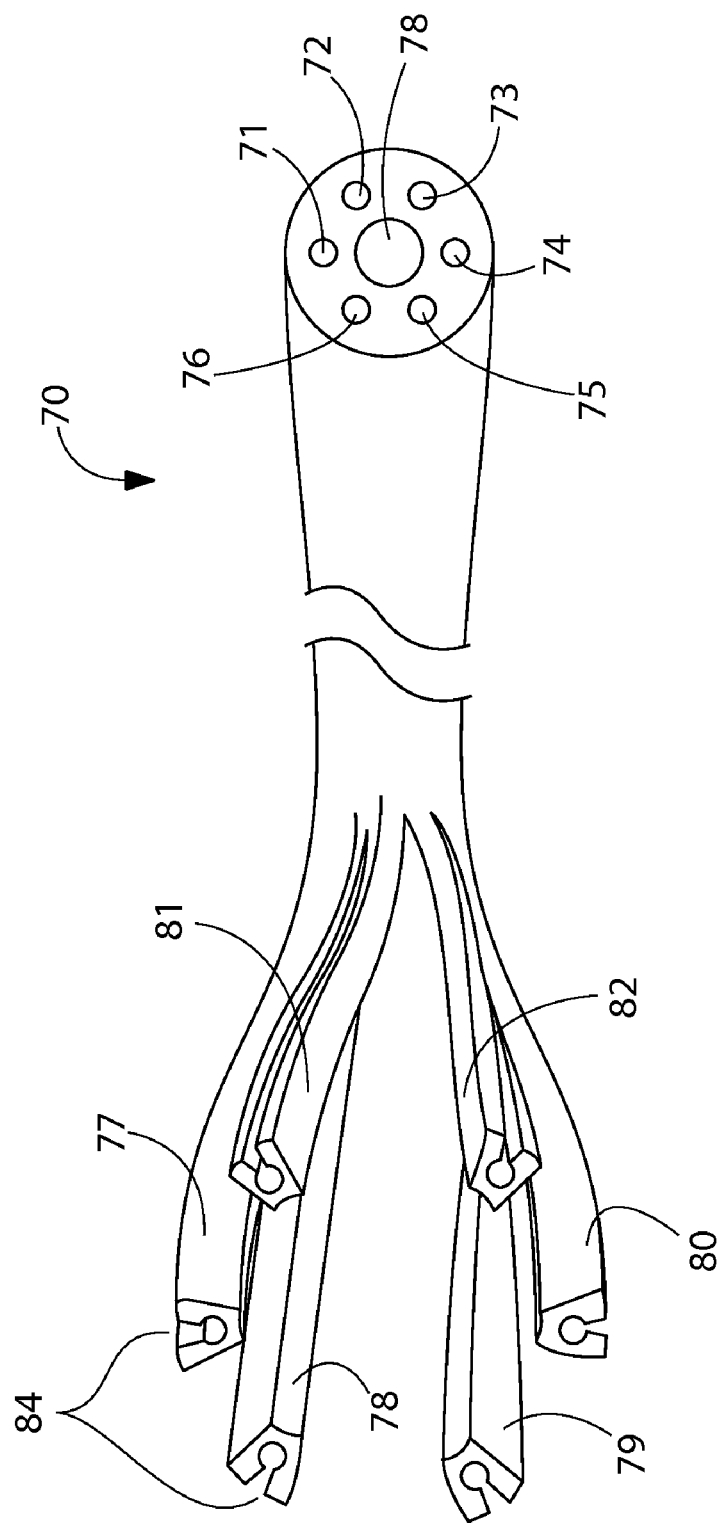
FIG. 5 is a perspective view of an alternate embodiment of an intake tube.

In the embodiment of the present invention thus described, the intake tube 14 has an oblong shape that contains four internal conduits. As has previously been mentioned, such a shape is merely exemplary. Referring to FIG. 5, an alternate embodiment of the intake tube 70 is shown. The intake tube 70 is initially molded into a round tube containing six small conduits 71, 72, 73, 74, 75, 76 and a large central conduit 78. The intake tube 70 is then sliced around the six small conduits 71, 72, 73, 74, 75, 76. This creates six arms 81, 77, 78, 79, 80, 82 from the initial tubing. A slice is further made into each of the six arms, therein exposing the small conduit 71, 72, 73, 74, 75, 76 along the length of the slice.

The purpose of FIG. 5 is to illustrate that the intake tube can have numerous internal and external shapes. Furthermore, the tubing can be repeatedly sliced to create multiple arms from the single tubing segment. The shape of the tubing exterior and interior depend upon the number of arms desired.

It will be understood that a person skilled in the art of tube extruding can make alternate embodiments of the present invention that are not illustrated. The external shape and internal configuration of the intake tube can be modified in many ways to produce any plurality of arms after slicing. All such variations, modifications, and alternate embodiments are intended to be included within the scope of the present invention as defined by the claims.

What is claimed is:

1. A method of producing a surgical drain tube, comprising the steps of:
   providing a length of extruded tubing that defines multiple internal conduits, wherein said length of extruded tubing has a first end and an opposite second end and said internal conduits run between said first end and said second end; and
   cutting slices in said length of extruded tubing into each of said multiple internal conduits, wherein each of said slices communicates with a different one of said internal conduits and runs from said first end to a termination point that is between said first end and said second end.

2. The method according to claim 1, further including the step of cutting said tubing into separate arms between said first end and said termination point.

3. The method according to claim 1, further including the step of providing a collection tube and joining said second end of said length of extruded tubing to said collection tube.

4. The method according to claim 3, wherein said collection tube defines a single conduit that communicates with said internal conduits of said length of extruded tubing.

5. The method according to claim 3, further including the step of providing a transition zone of between one inch and six inches exists on said length of extruded tubing between said termination point and said collection tube.

6. The method according to claim 2, further including the step of forming at least some of said separate arms to different lengths.

7. The method according to claim 1, wherein said step of cutting slices in said length of extruded tubing includes drawing part of said length of extruded tubing through at least one cutter.

* * * * *